(12) United States Patent
Fujimura et al.

(10) Patent No.: US 6,585,974 B1
(45) Date of Patent: Jul. 1, 2003

(54) PREVENTIVES FOR HEPATOPATHY

(75) Inventors: Katsuyuki Fujimura, Osaka (JP); Yasuyo Yamaguchi, Osaka (JP); Reiko Sugino, Osaka (JP); Hideki Shirogane, Osaka (JP); Toyomi Takeuchi, Osaka (JP)

(73) Assignees: Kobayashi Pharmaceutical Co., Ltd., Osaka (JP); Hitoshi Nagaoka, Chiba (JP)

( * ) Notice: Subject to any disclaimer, the term of this patent is extended or adjusted under 35 U.S.C. 154(b) by 0 days.

(21) Appl. No.: 09/856,759

(22) PCT Filed: Nov. 26, 1999

(86) PCT No.: PCT/JP99/06618

§ 371 (c)(1),
(2), (4) Date: Aug. 15, 2001

(87) PCT Pub. No.: WO00/32214

PCT Pub. Date: Jun. 8, 2000

(30) Foreign Application Priority Data

Nov. 27, 1998 (JP) ............................................. 10-338085

(51) Int. Cl.[7] ........................ A61K 35/84; A61K 47/00; A23K 1/165; A01N 25/00
(52) U.S. Cl. ................. 424/195.15; 424/439; 424/442; 514/893
(58) Field of Search ........................... 424/195.15, 439, 424/442; 514/893

(56) References Cited

FOREIGN PATENT DOCUMENTS

JP 58180428 * 10/1983
JP 062270532 11/1987

OTHER PUBLICATIONS

Sugano et al. ("Cancer Letters", 17,109 (1982).*
N. Sugano et al., Cancer Letters, 17:109–114 (1982).
Y. Suzuki et al., Nihon Daicho Kohmonbyo Kaishi, 43:178–191 (1990).
T. Tabata et al., Immunopharmacology, 24:57–63 (1992).
Y. Hibino et al., Immunopharmacology, 28:77–85 (1994).
M. Mitsuhashi–Kato et al., Plant Cell Physiol., 26(2):221–228 (1985).
Y. Mizoguchi et al., Kan Tan Sui, 15(1):127–135 (1987).
The Chinese Pharmaceutical Journal, vol. 30, No. 2, (1995), pp. 67–69.
The Journal of Pharmaceutical Practice, vol. 14, No. 1, (1996).
Chemical Abstracts, vol. 119, No. 1, p475, Jul. 5, 1993 abstract No. 119:458u.

* cited by examiner

*Primary Examiner*—Christopher R. Tate
*Assistant Examiner*—Randall Winston
(74) *Attorney, Agent, or Firm*—Birch, Stewart, Kolasch & Birch, LLP

(57) ABSTRACT

An agent protective against drug-induced hepatopathy containing Lentinus edodes mycelium extract.

9 Claims, 3 Drawing Sheets

PREVENTIVES FOR HEPATOPATHY

This application is the national phase under 35 U.S.C. §371 of PCT International Application No. PCT/JP99/06618 which has an International filing date of Nov. 26, 1999, which designated the United States of America and was not published in English.

FIELD OF THE INVENTION

The present invention relates to agents protective against hepatopathy. More specifically, it relates to agents protective against hepatopathy containing Lentinus edodes mycelium extract.

PRIOR ART

Shiitake (Lentinus edodes) is a common edible mushroom in both Japan and China, and has been cultivated in Japan for around 300 years. The part of the mushroom used as food consists of the reproductive body, also referred to as the fruiting body of fungi, and which produces spores, while the vegetative body includes hyphae which produce mycelia extending into a growing area such as soil or logs.

Shiitake has long been said to have some effect for against a variety of diseases and symptoms, but it is only relatively recently that any pharmacological effect has been described. Various effects of Lentinus edodes mycelium extract are reported. These include: the inhibition of oncogenesis and the growth of transplanted tumor cells in the large bowel and liver and increased survival of animals in carcinogenesis experiments in rats and mice (N. Sugano et al., Cancer Letter, 27:1, 1985; Y. Suzuki et al., Journal of the Japan Society of Coloproctology, 43:178, 1990, etc.); mitogenic activity (T. Tabata et al., Immunopharmacology, 24:57, 1992; Y. Hibino et al., Immunopharmacology, 28:77, 1994, etc.); enhanced antibody production and inhibitory effects against immunological hepatocyte damage caused by ADCC (antibody-dependent cell-mediated cytotoxicity) (Y. Mizoguchi et al., Journal of Hepato-Biliary-Pancreatic Study, 15:127, 1987); and plant hormone effects such as promoted rooting or growth of crops (M. Mitsuhashi-Kato et al., Plant Cell Physiol., 26:221, 1985) or anti-plant virus effects (Y. Komuro et al., Reports of Plant Virus Research Group of the Japan Ministry of Agriculture, Forestry and Fisheries, 1977).

An object of the present invention is to further explain the pharmacological actions of Lentinus edodes mycelium extract and to deduce new pharmaceutical or health care applications of Lentinus edodes mycelium extract.

DISCLOSURE OF THE INVENTION

As a result of detailed studies to solve the above problems, the present invention has been accomplished on the basis of the finding that Lentinus edodes mycelium extract shows a remarkable protective effect against drug-induced hepatopathy.

Accordingly, the present invention provides agents protective against drug-induced hepatopathy containing Lentinus edodes mycelium extract.

Agents protective against drug-induced hepatopathy of the present invention may be in the form of a composition for treating and/or preventing drug-induced hepatopathy comprising Lentinus edodes mycelium extract and optionally a pharmaceutically acceptable carrier.

Agents protective against drug-induced hepatopathy of the present invention may be in the form of either a food or a drink, but these forms are not limitative.

The present invention also provides methods for protecting against drug-induced hepatopathy comprising administering Lentinus edodes mycelium extract.

In addition the present invention also provides uses of Lentinus edodes mycelium extract for the preparation of a agent protective against drug-induced hepatopathy.

PREFERRED EMBODIMENTS OF THE INVENTION

Figure 1:
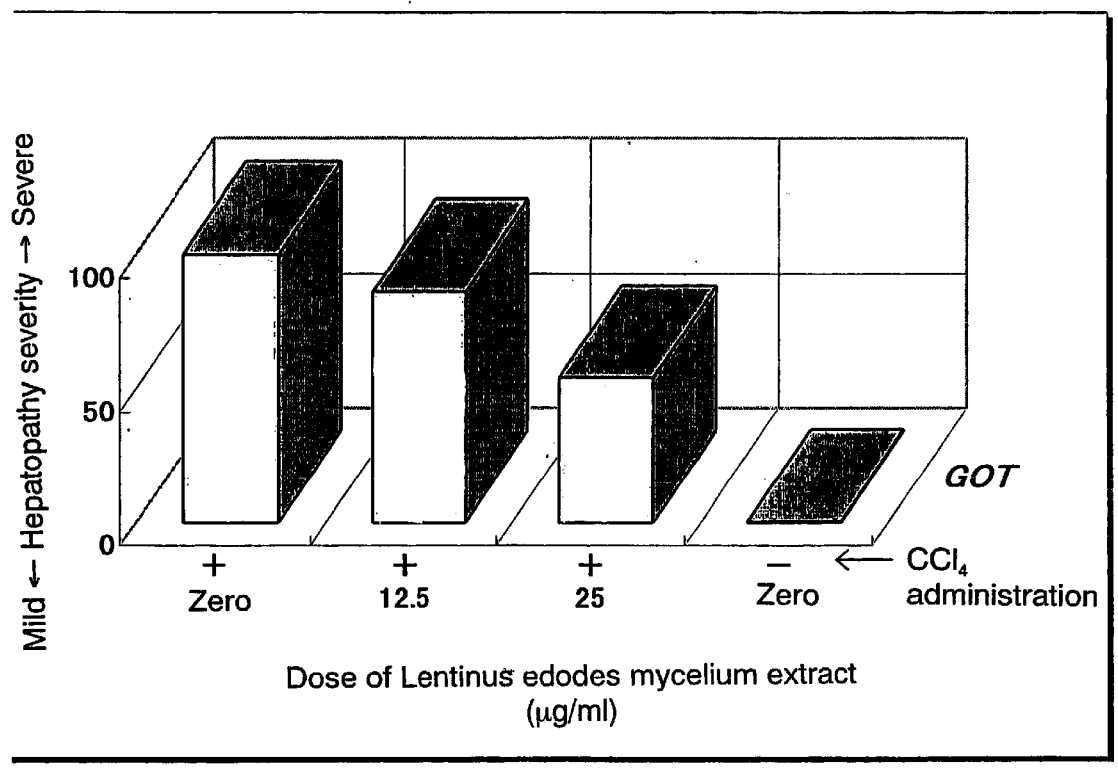
FIG. 1 is a graph showing the result of an in vitro hepatopathy protection test of Lentinus edodes mycelium extract using rat hepatocytes in primary culture.

Lentinus edodes mycelium extract used in agents protective against drug-induced hepatopathy of the present invention refers to an extract obtained by crushing and decomposing mycelia grown from Lentinus edodes spawn cultured on a solid medium, preferably by crushing and decomposing a solid medium containing Lentinus edodes mycelia in the presence of water and an enzyme.

Lentinus edodes mycelium extract used herein is preferably obtained by, but not limited to, the following process. Lentinus edodes spawn is inoculated on a solid medium based on bagasse (sugar cane residue) and defatted rice bran to grow mycelia, and then the solid medium containing the grown mycelia is delignified so that 30% by weight or less is able to pass through a 12-mesh sieve. To this delignified solid medium are added water and one or more enzymes selected from cellulase, protease or glucosidase while maintaining the solid medium at a temperature of 30–55° C., and said solid medium is crushed and ground in the presence of said enzyme so that at least 70% by weight of bagasse fiber is able to pass through a 12-mesh sieve. Then, the temperature is raised to 95° C. to ensure deactivation of the enzyme and sterilization, and the resulting suspension is filtered to give Lentinus edodes mycelium extract. Lentinus edodes mycelium extract may be used directly in the protective agents of the present invention, but also can be concentrated and freeze-dried as a powder to be stored, and used conveniently in various forms. Freeze-dried powder is brown, hygroscopic and has a peculiar taste and odor.

Thus obtained Lentinus edodes mycelium extract contains 15–50%, preferably 20–40% (w/w) carbohydrates determined by the phenol-sulfuric acid method, 10–40%, preferably 13–30% (w/w) proteins determined by the Lowry method and 1–5%, preferably 2.5–3.5% (w/w) polyphenols determined by the Folin-Denis method using gallic acid as a standard. Lentinus edodes mycelium extract further contains, but is not limited to, about 0.1% fat, about 0.4% fiber and about 20% ash.

An example of the sugar composition (%) of Lentinus edodes mycelium extract is as follows though it can vary depending on culture conditions or the like: xylose 15.2, arabinose 8.2, mannose 8.4, glucose 39.4, galactose 5.4, galactosamine 12.0, glucuronic acid 11.3.

Lentinus edodes mycelium extract showed remarkable protective effects against drug-induced hepatopathy in all of the following tests: an in vitro test using rat hepatocytes, an in vivo test using CCl$_4$-induced rat hepatopathy and a test on human patients with drug-induced hepatopathy.

Protective agents of the present invention are useful for hepatopathy induced by antibiotics such as cephems (eg, Cefroxadine, Cefuroxime Sodium, Latamoxef Sodium), aminoglycosides (eg, Amikacin Sulfate), antitumors (eg, Aclarubicin), acid-fast bacterial antibiotics (eg, Rifampicin), tetracyclines, macrolides, penicillins; central nervous system agents such as antipyretic, analgesic and antiphlogistic drugs (eg, Aspirin), tranquilizers (eg, cloxazolam), antiepileptic drugs (eg, sodium valproate), general anesthetics (eg, Halothane), sedative hypnotics (eg, phenobarbital); common cold drugs; circulatory drugs such as antiarrhythmics (eg, pindolol), vasodilators (eg, Trapidil), circulatory drugs (eg, nicardipine hydrochloride), antihypertensives (eg, labetalol hydrochloride), antiarteriosclerotics (eg, clofibrate); antimetabolites such as tegafur; hormone drugs such as estracyt; sulfa drugs such as sulfamethoxazole; antituberculous drugs such as isoniazid; synthetic antibacterials such as norfloxacin; and so-called environmental hormones such as bisphenols, phthalate esters, vinyl chloride monomers, nonylate esters, and alcohols. Thus, protective agents of the present invention can be used as a composition for treating and/or preventing drug-induced hepatopathy comprising Lentinus edodes mycelium extract and optionally a pharmaceutically acceptable carrier.

They are most preferably administered via the oral route, but may also be administered via intravenous, subcutaneous or other route. Dosage forms suitable for oral administration include, but are not limited to, tablets, capsules, powders, granules, solutions, syrups, etc.

Pharmaceutically acceptable carriers include, but are not limited to, suitable excipients, binders, disintegrators, lubricants, flavoring agents, colorants, solubilizers, suspending agents, coating agents or the like known in the art.

The dose of protective agents of the present invention can be determined by physicians, pharmacists or dietitians taking into account the age, weight and condition of the patient, the route of administration and other factors. The dose is not strictly limited because Lentinus edodes mycelium extract contained in the protective agents of the present invention is very safe and is used for food, but normally corresponds to 40 mg–6 g, preferably 400 mg–1.8 g daily expressed as Lentinus edodes mycelium powder. It may be administered concurrently with drugs causative of hepatopathy.

Protective agents of the present invention can also be provided in the form of a food. Preferred forms of food include granules, noodles, candies, jellies, cookies, etc. Protective agents of the present invention can also be provided in the form of a drink. These foods or drinks may contain vitamins, minerals such as calcium, dietary fibers such as chitosan, proteins such as soybean extract, fats such as licithin, sugars such as lactose in addition to Lentinus edodes mycelium extract.

The following examples further illustrate the present invention without, however, limiting the scope of the invention thereto. Various changes and modifications can be made by those skilled in the art and these changes and modifications are also included in the present invention.

EXAMPLES

Example 1

Preparation Process of Lentinus Edodes Mycelium Extract

A solid medium consisting of 90 parts by weight of bagasse and 10 parts by weight of rice bran was soaked in an appropriate amount of pure water, and then inoculated with Lentinus edodes spawn and allowed to stand in an incubator at controlled temperature and humidity to grow mycelia. After mycelia spread over the solid medium, the bagasse base was delignified so that 24% by weight or less was able to pass through a 12-mesh sieve. To 1.0 kg of this delignified medium were added 3.5 kg of pure water and 2.0 g of purified cellulase while maintaining the solid medium at 40° C., to prepare a medium-containing mixture.

Then, the medium-containing mixture was circulated using a variable speed gear pump, and the solid medium was crushed and ground under the gears for about 200 minutes, to enable about 80% by weight of bagasse fiber to pass through a 12-mesh sieve. The medium-containing mixture was crushed and ground while the temperature of said mixture was gradually increased. Then, the medium-containing mixture was further heated to 90° C. and allowed to stand for 30 minutes. Heating to 90° C. ensured deactivation of the enzyme and sterilization. The resulting medium-containing mixture was filtered through a 60-mesh filter cloth to give a Lentinus edodes mycelium extract liquid, which was concentrated and then converted into freeze-dried powder.

Example 2

In Vitro Test Using Hepatocytes in Primary Culture

1) Isolation and Primary Culture of Rat Hepatocytes

Hepatocytes were isolated from rats (male Wistar, 6–8 weeks old) and cultured at 37° C. under 5% CO$_2$ overnight.

2) Treatment of Hepatocytes With CCl$_4$ and Test Materials

Hepatocytes prepared in 1) were incubated for 24 hours with 500 μl of a serum-free medium containing CCl$_4$ (DMSO solution: hepatopathy-inducer) and a test material (Lentinus edodes mycelium extract or a control material) at various concentrations.

3) Determination of GOT Activity

The culture supernatant was transferred to an Eppendorf tube and centrifuged at 10000 rpm for 5 minutes at room temperature. GOT activity in this supernatant was determined with a GOT reagent (Liqui Tech GOT IFCC from Boehringer Mannheim). Hepatopathy severity was assessed by calculating the percentage of GOT activity in each culture supernatant based on the average GOT activity in the culture supernatant not containing any test material. The results are shown in FIG. 1.

As shown in FIG. 1, Lentinus edodes mycelium extract was found to exhibit a protective effect against hepatopathy.

Example 3

In Vivo Test Using CCl$_4$-incuced Rat Hepatopathy

Lentinus edodes mycelium extract granules containing 20% of Lentinus edodes mycelium extract powder (with the balance lactose) were prepared and orally administered to rats for 7 days to examine the protective effect against CCl$_4$-induced hepatopathy. After completion of the administration, CCl$_4$ was intraperitoneally administered to induce hepatopathy, and then blood was collected from abdominal aorta to determine GOT and GPT in serum. The results are shown in FIG. 2.

Figure 2:
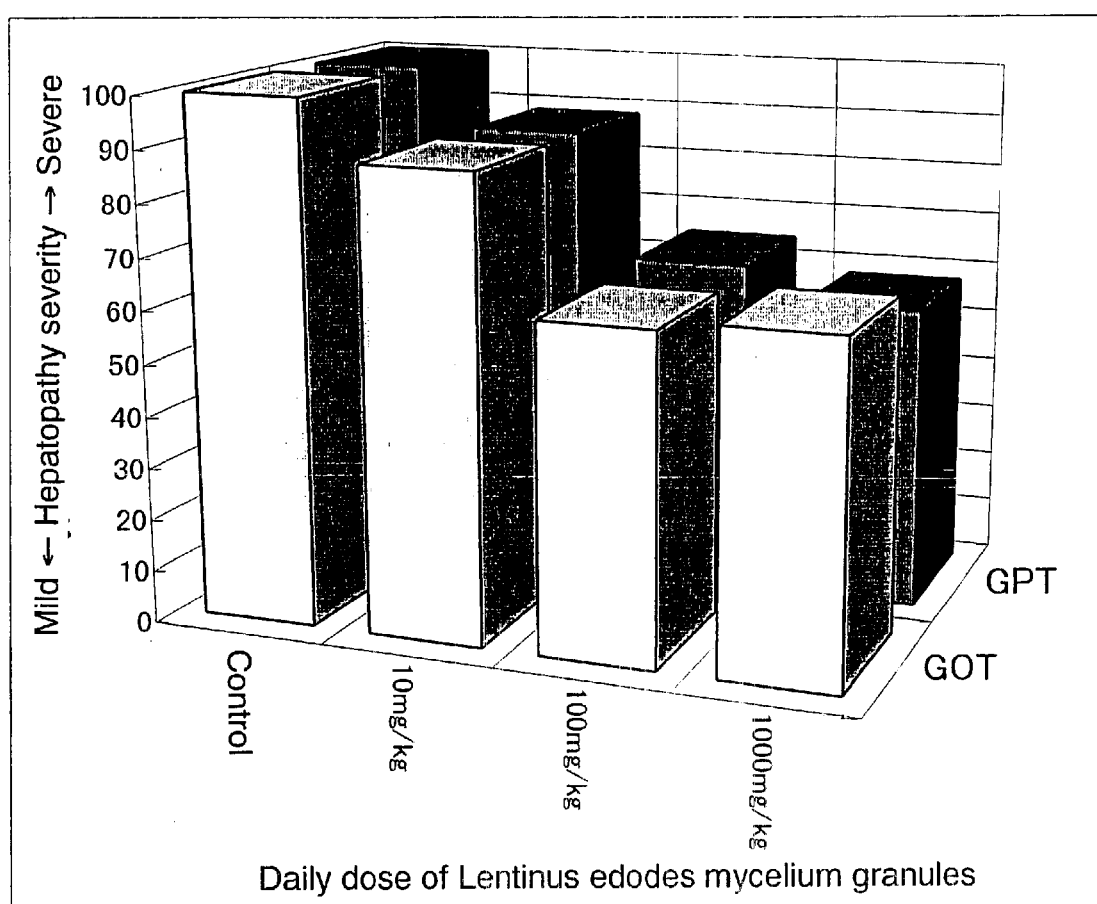
FIG. 2 is a graph showing the result of an in vivo hepatopathy protection test of Lentinus edodes mycelium extract using $CCl_4$-induced rat hepatopathy.

As shown in FIG. 2, Lentinus edodes mycelium extract was found to exhibit a protective effect against hepatopathy.

Example 4

Test on Human Patients With Drug-Induced Hepatopathy

Figure 3:
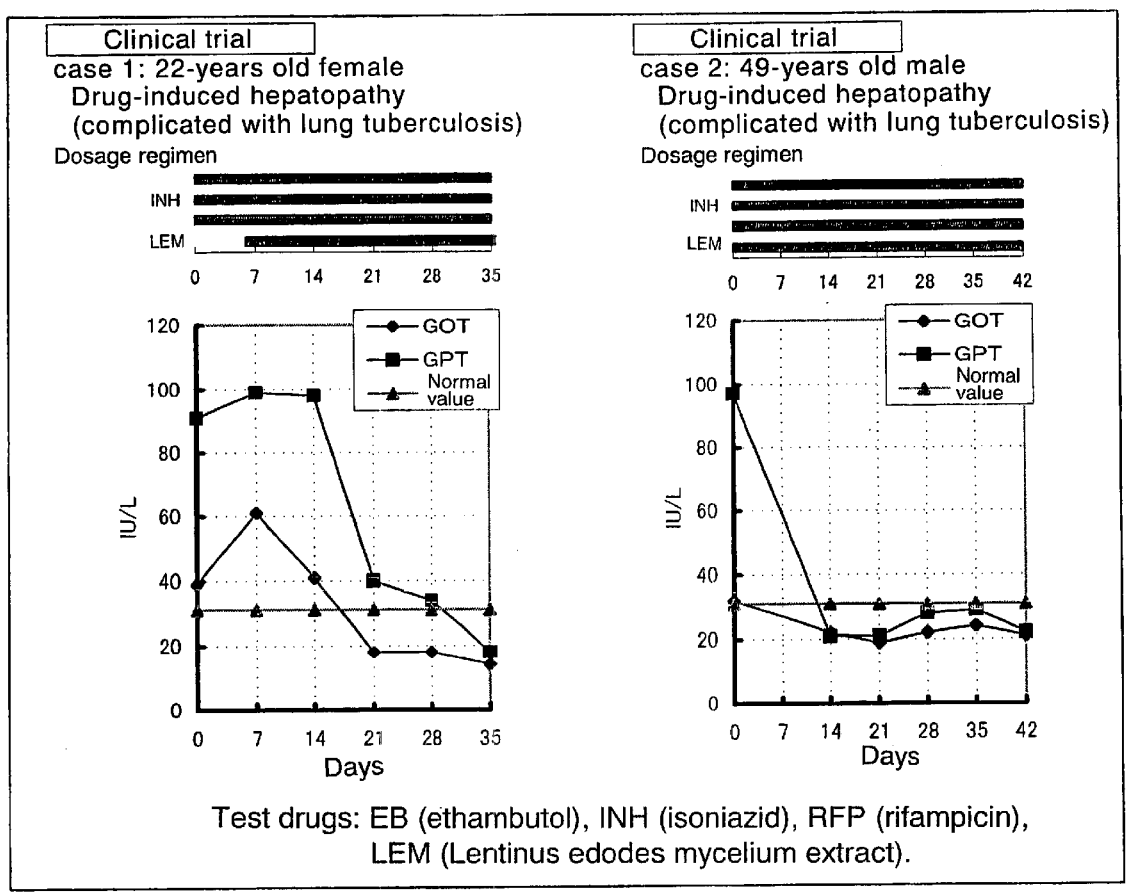
FIG. 3 is a graph showing the result of a hepatopathy protection test of Lentinus edodes mycelium extract on human patients with drug-induced hepatopathy.

Two human patients having hepatopathy induced by chemotheraphy (both complicated with lung tuberculosis)

daily received 6 g of Lentinus edodes mycelium extract granules (containing 20% of Lentinus edodes mycelium extract powder with the balance lactose) for 4 weeks. Drugs causative of hepatopathy (ethambutol, isoniazid, rifampicin) were continuously administered. After 4 weeks, GOT and GPT levels in peripheral blood of the patients were measured. The results are shown in FIG. 3. The levels of GOP and GPT in both patients dropped into the normal range. No side-effects were observed.

INDUSTRIAL APPLICABILITY

Agents protective against drug-induced hepatopathy containing Lentinus edodes mycelium extract of the present invention can be used to both prevent or treat hepatopathy induced by medication. Protective agents of the present invention are capable of a wide range of industrial application because they can be used concurrently with drugs causative of hepatopathy, and can also be used safely without any side-effects.

What is claimed is:

1. A method for protecting against drug-induced hepatopathy comprising:
    administering to a patient in need thereof an effective amount of Lentinus edodes mycelium extract, wherein said Lentinus edodes mycelium extract is obtained by crushing and decomposing mycelia grown from Lentinus edodes spawn cultured on a solid medium based bagasse in the presence of water and one or more enzymes selected from the group consisting of cellulase, protease and glucosidase.

2. A method for treating and/or protecting against drug-induced hepatopathy comprising:
    administering to a patient in need thereof an effective amount of Lentinus edodes mycelium extract, wherein said Lentinus edodes mycelium extract is obtained by crushing and decomposing mycelia grown from Lentinus edodes spawn cultured on a solid medium based on bagasse in the presence of water and one or more enzymes selected from the group consisting of cellulase, protease and glucosidase.

3. The method of claim 1 or 2 wherein Lentinus edodes mycelium extract is administered in a form of a composition comprising Lentinus edodes mycelium extract and a pharmaceutically acceptable carrier.

4. The method of claim 1 or 2 wherein Lentinus edodes mycelium ectract is administered orally.

5. The method of claim 4 wherein Lentinus edodes mycelium extract is administered in a form of a food.

6. The method of claim 4 wherein Lentinus edodes mycelium extract is administered in a form of a drink.

7. A method for treating drug-induced hepatopathy comprising:
    administering to a patient in need thereof an effective amount of Lentinus edodes mycelium extract, wherein said Lentinus edodes mycelium extract is obtained by crushing and decomposing mycelia grown from Lentinus edodes spawn cultured on a solid medium based on bagasse in the presence of water and one or more enzymes selected from the group consisting of cellulase, protease and glucosidase.

8. The method of claim 7, wherein said extract is administered orally.

9. The method of claim 7, wherein said patient is suffering from hepatopathy induced by an agent selected from the group consisting of an antibiotic, a central nervous system agent, a common cold drug, an antimetabolite, a hormone drug, a sulfa drug, a synthetic antibacterial, and an environmental hormone.

* * * * *